(12) United States Patent
Pardoll et al.

(10) Patent No.: US 8,696,663 B2
(45) Date of Patent: Apr. 15, 2014

(54) ELECTROMECHANICAL POLYP SNARE

(75) Inventors: Peter Pardoll, Treasure Island, FL (US);
Richard Pfahl, Acworth, GA (US);
Wolfgang Sembach, Seminole, FL (US);
Arik Zoran, Clearwater, FL (US)

(73) Assignee: Bovie Medical Corporation,
Clearwater, FL (US)

( * ) Notice: Subject to any disclaimer, the term of this patent is extended or adjusted under 35 U.S.C. 154(b) by 1255 days.

(21) Appl. No.: 11/650,837

(22) Filed: Jan. 8, 2007

(65) Prior Publication Data

US 2008/0167661 A1 Jul. 10, 2008

(51) Int. Cl.
*A61B 18/18* (2006.01)
*A61B 17/24* (2006.01)

(52) U.S. Cl.
USPC .............. 606/47; 606/110; 606/111; 606/113

(58) Field of Classification Search
USPC .................................. 606/14, 46–47, 49, 110
See application file for complete search history.

(56) References Cited

U.S. PATENT DOCUMENTS

| | | | |
|---|---|---|---|
| 3,955,578 A * | 5/1976 | Chamness et al. ............... 606/47 |
| 4,294,254 A * | 10/1981 | Chamness ....................... 606/47 |
| 5,078,716 A * | 1/1992 | Doll ................................. 606/47 |
| 5,084,054 A * | 1/1992 | Bencini et al. ................. 606/113 |
| 5,116,332 A * | 5/1992 | Lottick ............................ 606/42 |
| 5,376,094 A * | 12/1994 | Kline .............................. 606/113 |
| 6,287,304 B1 * | 9/2001 | Eggers et al. ................... 606/37 |
| 6,352,539 B1 * | 3/2002 | Avellanet ....................... 606/113 |
| 2001/0049524 A1 * | 12/2001 | Morgan et al. .................. 606/50 |

* cited by examiner

*Primary Examiner* — Linda Dvorak
*Assistant Examiner* — Jaymi Della
(74) *Attorney, Agent, or Firm* — Gerald E. Hespos; Michael J. Porco; Matthew T. Hespos (57) ABSTRACT

An electrosurgical device is provided for removing polyps from the gastrointestinal tract of a patient. In one implementation, an electrosurgical device comprises a snare support member and a snare positioning assembly mounted on an exterior surface of the snare support member. The snare positioning assembly has a longitudinal axis substantially parallel with and offset from the longitudinal axis of the snare support member. The device also includes a base member attached to a distal end of the snare support member and has a longitudinal axis substantially aligned with the longitudinal axis of the snare support member. An aperture is formed through a side wall of the base member. Also included is a polyp snare extending through a first channel of the snare positioning assembly, through the aperture, and through a second channel of the base member.

20 Claims, 7 Drawing Sheets

ELECTROMECHANICAL POLYP SNARE

BACKGROUND OF THE INVENTION

1. Field of the Invention

An electrosurgical device for use with an electrosurgical generator to remove polyps from the gastrointestinal tract.

2. Description of the Prior Art

Electrosurgical generators used in cutting and coagulating have become common place. Such devices include electrosurgical polyp snares for use in removing polyps found in the gastrointestinal tract. Such surgical snares generally include an elongated flexible sheath connected to an operating hand piece. Extending through the sheath is an elongated flexible cable including an operating loop coupled to a movable portion of the operating hand piece so that the cable can be extended and retracted by a surgeon relative to the elongated flexible sheath to selectively open and close the operating loop as the surgeon manipulates the extended operating hand piece to protract or retract the cable. When the cable is in extended position the operating loop is fully employed outside the elongated flexible sheath and in its fully extended position. As the cable is retracted the operating loop is drawn into the elongated flexible sheath and closed around the polyp.

U.S. Pat. No. 4,256,113 and U.S. Pat. No. 4,294,254 show a surgical cannula including a sheath having a member movably disposed therein. With a surgical instrument operable by movement of the movable member relative to the sheath. The cannula further includes an operating assembly comprising a body or handle which slidably receives a slide for movement of the body including a pair of longitudinally spaced apart walls having the same general shape as the cross section of the body. The walls are provided with aligned apertures which rotatably receive a stem. The stem includes proximal and distal ends, and the proximal end of the movable member is fixedly attached to the distal end of the stem. The proximal end of the sheath is fixedly attached to the body portion of the handle. The stem is provided with a thumbwheel which is accessible through the side wall of the body being manipulatable to rotate the movable member in the sheath. The slide includes a rack and the body supports an additional thumbwheel having pinion gear teeth formed thereon, the pinion gear teeth engaging the rack. Manipulation of the second-mentioned thumbwheel causes the slide to move longitudinally within the body to move the movable member longitudinally within the sheath.

U.S. Pat. No. 6,346,106 relates to a surgical instrument including a body including a passageway, a snare electrode, a spool and an electrical connector. The snare electrode. A second portion of the snare electrode is extendable from passageway for forming a loop sized to be placed over tissue (e.g., portion(s) of the uterus and/or kidney(s), spleen, pancreas, gallbladder, remnant from the liver, and/or vascular aneurysm) to be removed from a patient. The spool is rotatably supported in a proximal part of the body. A first portion of the snare electrode is windable about the spool. A rotation of the spool in a winding direction causes retraction of the first portion of the snare electrode from a first port of the passageway thereby closing the loop to engage the tissue.

U.S. Pat. No. 4,293,752 shows a ribbon switch assembly including a tape switch strip.

U.S. Pat. No. 4,552,143 relates to a removable switch electrocautery instrument, comprising a releasably mounting switch means with a conductive member adapted to come into contact with living tissue and a handle member. Means are provided on the switch means to make an electrical connection with the conductive member adapted to come into contact with the living tissue. Electrical connection between the switch means may be made through one of the springably releasable attachments or a separate connector element.

U.S. Pat. No. 5,304,763 shows an electrosurgical hand piece of different-sized electrodes having hollow shanks and means for supplying suction adjacent the electrode tip for simultaneous removal of liquids or gasses. The hand piece can be fitted with a removable finger switch activator which can also be attached to other objects for the surgeon's convenience. Means for controlling the suction pressure at the electrode tip are also provided.

U.S. Pat. No. 5,433,702 shows a hand piece operatively coupled to a phacoemulsification machine to supply the hand piece with irrigation fluid, aspiration suction and ultrasonic energy. The application of irrigation fluid and aspiration suction to the hand piece are preferably controlled with a foot pedal which is operatively coupled to the phacoemulsification machine. The application of ultrasonic energy to the hand piece is controlled by a button, slide tab, knob or the like which is preferably detachably mounted to the main body of the hand piece so that the application of ultrasonic energy can be manually controlled by the surgeon.

Many of the prior art surgical snares are difficult to manipulate with precision at the point of application. In addition, control of the various operating modes through hand and foot switches is unnecessarily awkward.

SUMMARY OF THE INVENTION

The present invention relates to an electrosurgical device for use with an electrosurgical generator to remove polyps from the gastrointestinal tract of a patient.

The electrosurgical device comprises a hand piece, a snare positioning assembly and polyp snare.

The hand piece comprises a body or housing and a snare support member attached thereto.

The polyp snare extending from the snare positioning assembly through the snare support comprises an electrically nonconductive sheath having an electrically conductive snare wire terminating in a polyp snare or loop slidably disposed therein.

The snare positioning assembly comprises a drive motor operatively coupled to a positioning slide to extend and retract the polyp snare or loop within the gastrointestinal tract of patient for removal of a polyp therefrom.

The invention accordingly comprises the features of construction, combination of elements, and arrangement of parts which will be exemplified in the construction hereinafter set forth, and the scope of the invention will be indicated in the claims.

BRIEF DESCRIPTION OF THE DRAWINGS

For a fuller understanding of the nature and object of the invention, reference should be had to the following detailed description taken in connection with the accompanying drawings in which.

Similar reference characters refer to similar parts throughout the several views of the drawings.

DETAILED DESCRIPTION OF THE INVENTION

Figure 1:
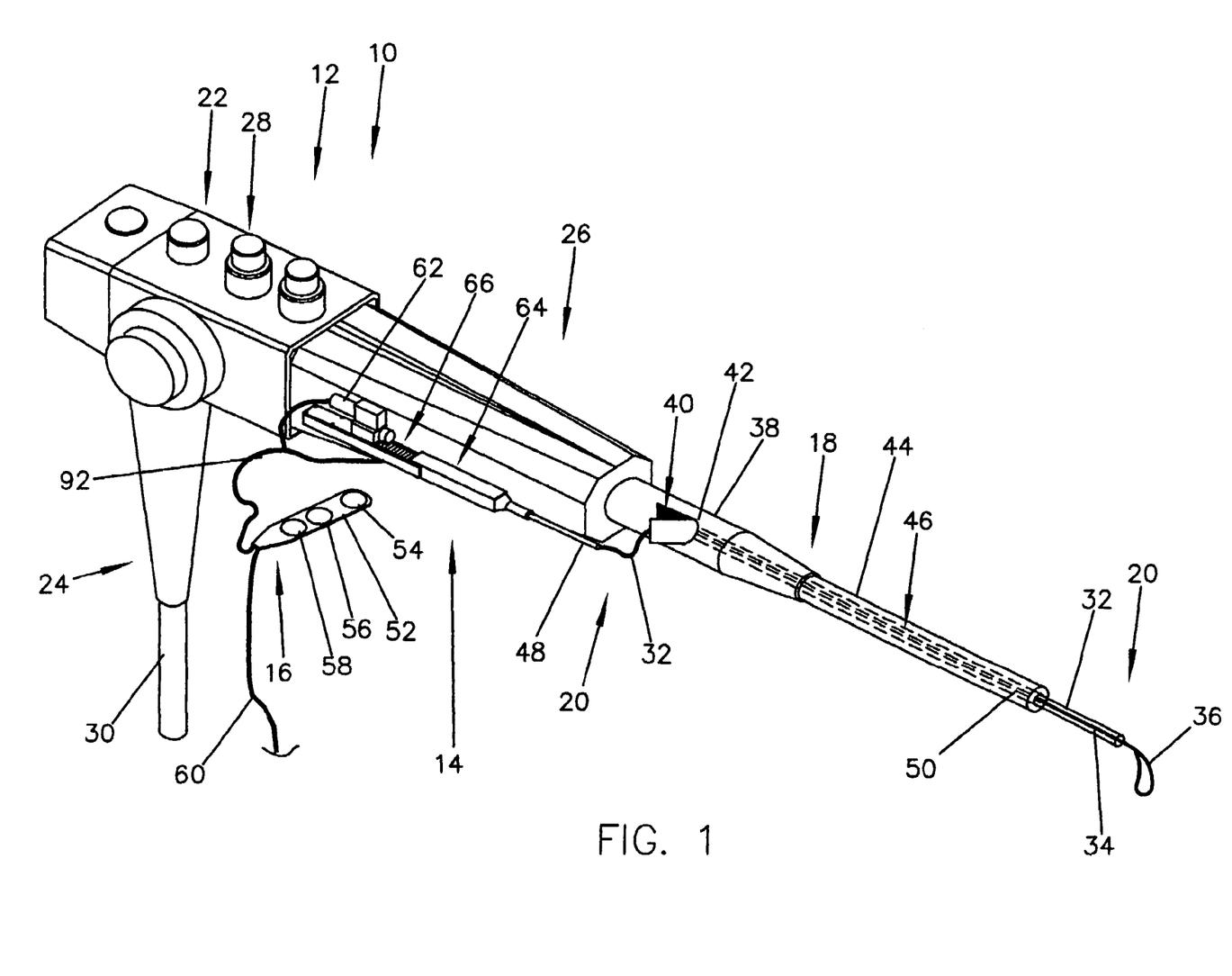
FIG. 1 is a perspective view of the electrosurgical device of the present invention.

As shown in FIG. 1, the present invention relates to an electrosurgical device generally indicated as 10 for use with an electrosurgical generator (not shown) to remove polyps from the gastrointestinal tract of a patient.

The electrosurgical device 10 comprises a hand piece, a snare positioning assembly, a remote or auxiliary switch assembly, a snare support and polyp snare generally indicated as 12, 14, 16, 18 and 20 respectively.

The hand piece 12 comprises a body or housing generally indicated as 22 having an operator handle generally indicated as 24 and a snare support member generally indicated as 26 attached to the lower portion and the front portion thereof respectively. A conventional switch arrangement generally indicated as 28 that can alternately be used to control operation of the electrosurgical device 10 is mounted on the top of the body or housing 22. The switch arrangement 28 is coupled or connected to the electrosurgical generator (not shown) by an electrosurgical generator cable 30.

The snare positioning assembly 14 and the snare support 18 are attached to or mounted on the snare support member 26 respectively.

As shown in FIG. 1, the polyp snare 20 extending from the snare positioning assembly 14 through the snare support 18 as described more fully herewith comprises an electrically nonconductive sheath 32 having an electrically conductive snare wire 34 terminating in a polyp snare or loop 36 slidably disposed therein.

As shown in FIG. 1, the snare support 18 comprises a proximal hollow base member 38 including a snare aperture or opening 40 formed through a side wall 42 thereof and a distal flexible elongated snare guide 44 having a snare channel 46 formed therethrough such that the electrosurgical nonconductive sheath 32 and the electrically conductive snare wire 34 extend from the forward or distal end portion 48 of the snare positioning assembly 14 through the snare aperture or opening 40 and the snare channel 46 through the forward distal end portion 50 of the distal flexible elongated snare guide 44.

As shown in FIGS. 1 through 4, the remote or auxiliary switch assembly 16 comprises a switch pad 52 to operatively support an electrosurgical generator control switch 54 to selectively activate the electrosurgical generator (not shown), a snare positioning switch 56 to selectively control operation of the snare positioning assembly 14 to extend and retract the electrically conductive snare wire 34 and the electrically conductive polyp loop 36, and a polyp cutting switch 58 to selectively feed current through the electrically conductive snare wire 34 and electrically conductive polyp loop 36 when disposed in surrounding relationship relative to a polyp to be removed from the gastrointestinal tract of a patient. The switches 54, 56 and 58 are coupled to the electrosurgical generator (not shown) by a corresponding conductor disposed with a conductor cable 60.

Figure 2:
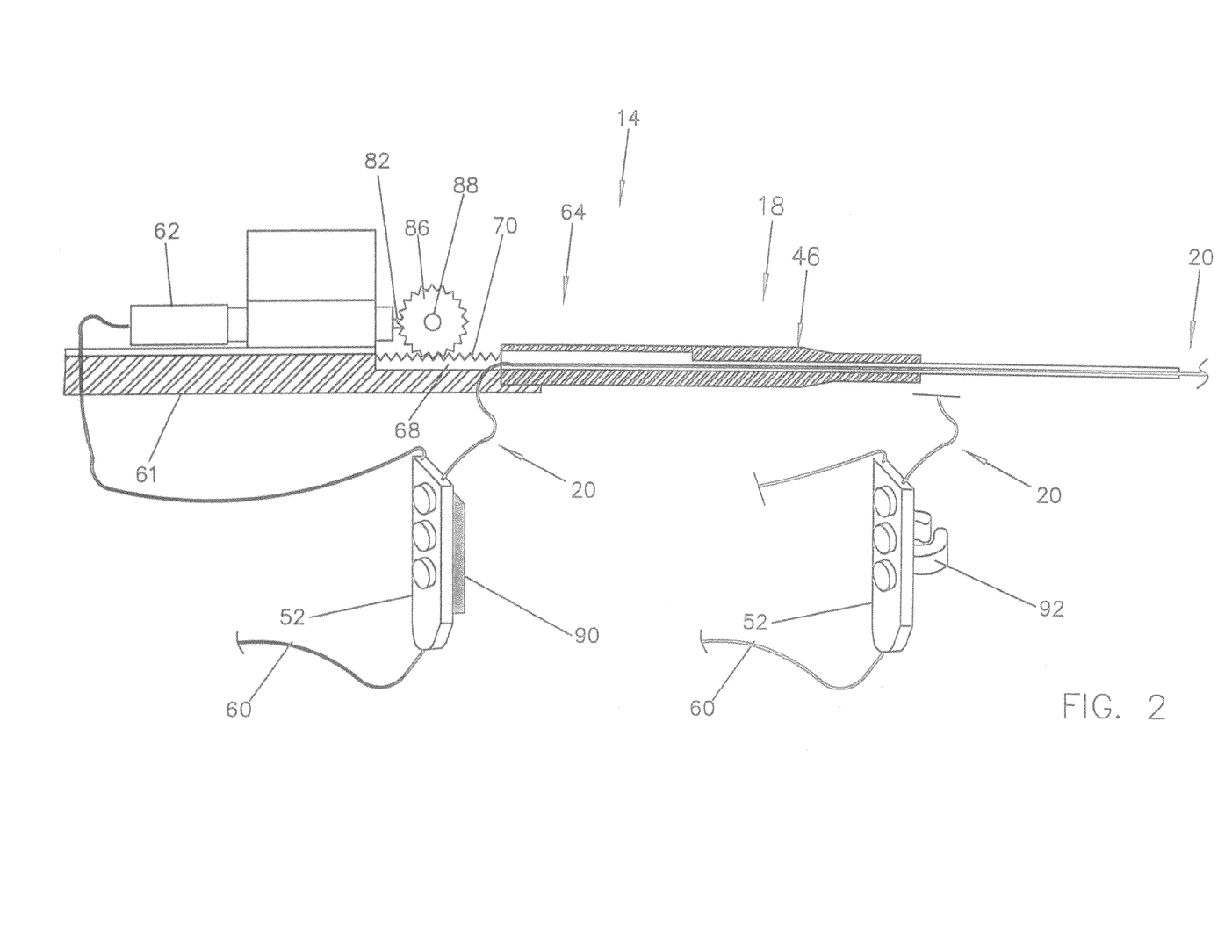
FIG. 2 is a partial cross-sectional side view of the snare guide and the snare positioning assembly of the present invention.
Figure 3:
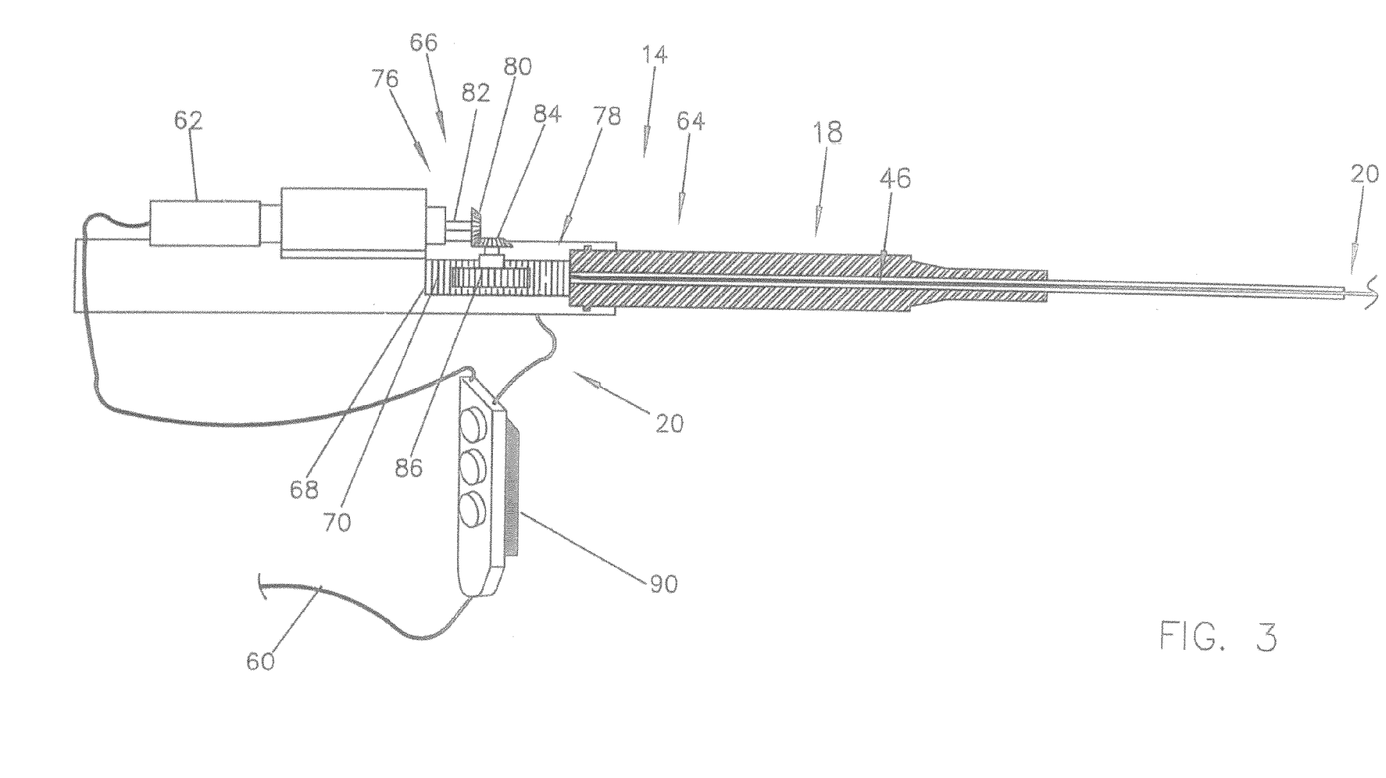
FIG. 3 is a partial cross-sectional top view of the snare guide and the snare positioning assembly of the present invention.
Figure 4:
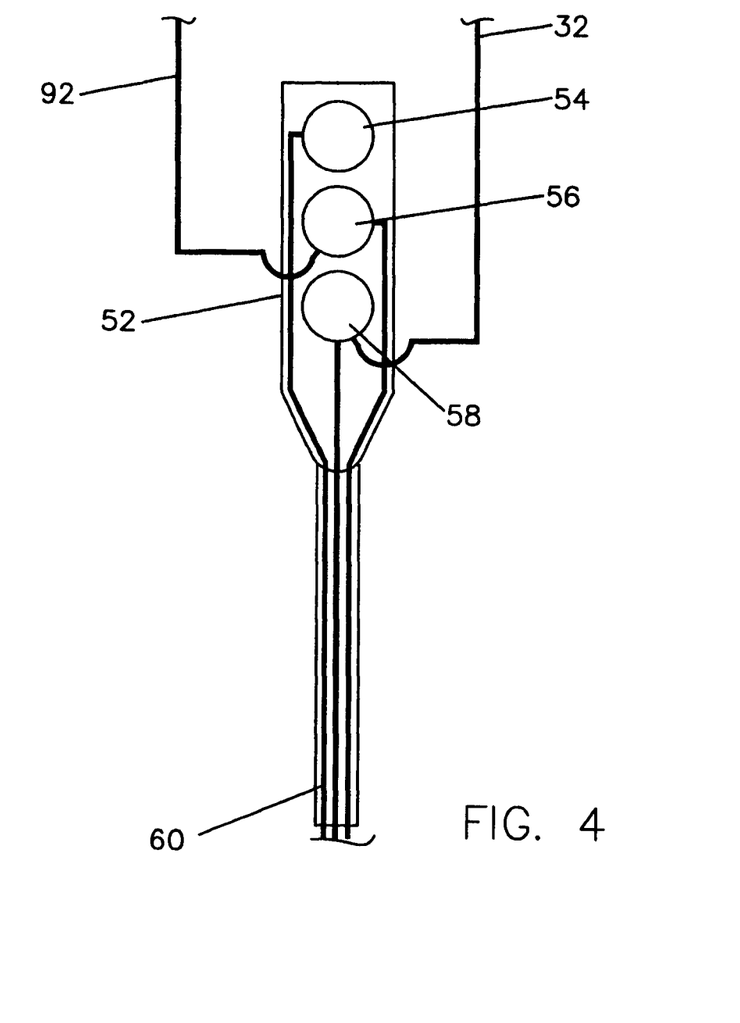
FIG. 4 is a detail view of the remote or auxiliary switch of the present invention.

As best shown in FIGS. 2 and 3, the snare positioning assembly 14 comprises a reversible drive motor 62 operatively coupled to a positioning slide generally indicated as 64 by an intermediate drive mechanism generally indicated as 66. The positioning slide 64 comprises a slide rack 68 including a plurality of teeth 70 formed on the upper surface of the distal portion thereof. The proximate hollow base member 38 comprises a snare support generally indicated as 72 having a snare channel 74 formed therethrough to slidingly receive a portion of the polyp snare 20 when the polyp snare 20 is directed into the snare aperture or opening 40. The intermediate drive mechanism 66 comprises a first drive section generally indicated as 76 and a second drive section generally indicated as 78 disposed to operatively engage each other to extend and retract the positioning slide 64 and the polyp snare 20 through the snare channel 46 to position the polyp snare or loop 36 within the gastrointestinal tract of patient for removal of a polyp therefrom.

Specifically, the first drive section 76 comprises a drive gear 80 coupled to the reversible drive motor 62 by a drive shaft 82; while, the second drive section 78 comprises a first drive gear 84 in operatively engagement with the drive gear 80 and a second drive gear 86 coupled thereto by a connecting shaft 88 in operative engagement with the teeth 70 of the slide rack 68 to move the positioning slide 64 and the snare support 72 in response to operation of the reversible drive motor 62 to advance and withdraw the polyp snare 20 through the snare aperture or opening 40 and the snare channel 46.

In use, the switch pad 52 of the remote or auxiliary switch assembly 16 may be attached to the hand piece 12 with a self-adhesive strip 90 or attached to a cable or other portion of the electrosurgical device 10, electrosurgical generator (not shown) or accessory by a clip or device 92 such as a loop or clamping element or fingers as shown in FIG. 2.

The electrosurgical generator control switch 54 and the polyp cutting switch 58 can each comprise a two position on-off contact switch; while the snare positioning switch 56 may comprise a three position contact switch to control the operating direction of the reversible motor 62 to control the direction of travel of the polyp snare 20.

In operation, as shown in FIG. 1, the switch assembly 16 mounts on the electrosurgical hand piece handle 10 or the other portion of the electrosurgical device 10. It can be easily positioned to any location convenient to the surgeon where he or she can easily manipulate the switches 54, 56 and 58 with one or two fingers to control the application of electrosurgical energy to the polyp snare or loop 36 electrode.

The electrosurgical generator (not shown) is controlled or activated by depressing the electrosurgical generator control switch 54.

The electrosurgical device 10 is held by the surgeon to position the polyp snare 20 by inserting the distal end portion of the electrically nonconductive sheath 32 and electrically conductive snare wire 34 with the polyp snare or loop 36 extending therefrom into the gastrointestinal tract of the patient. The polyp snare or loop 36 is manipulated relative to the polyp by the snare position switch 56. Once the polyp snare or loop 36 is positioned around the polyp, the polyp cutting switch 58 is turned on to feed cutting power or current from the electrosurgical generator (not shown) through the electrically conductive snare wire 34 to the polyp snare or loop 36 to cut the polyp from the intestinal wall. Power to the electrically conductive snare wire 34 and the polyp snare or loop 36 is turned off by depressing the polyp cutting switch 38. The polyp snare 20 is then withdrawn from the gastrointestinal tract by activating the reversible drive motor 62 by depressing the snare positioning switch 56.

Figure 5:
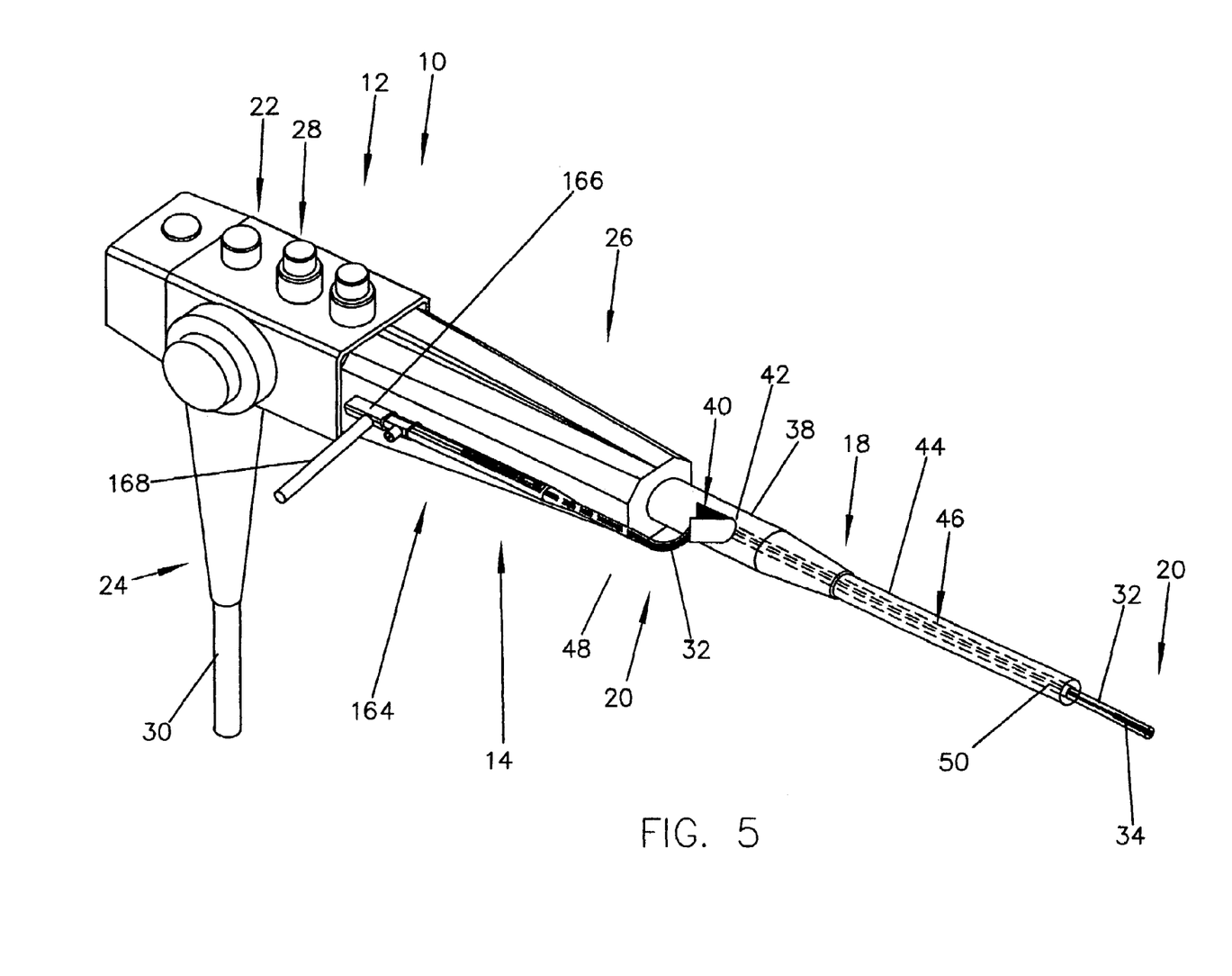
FIG. 5 is a perspective view of the electrosurgical device of the present invention with an alternate embodiment of the snare positioning assembly.
Figure 6:
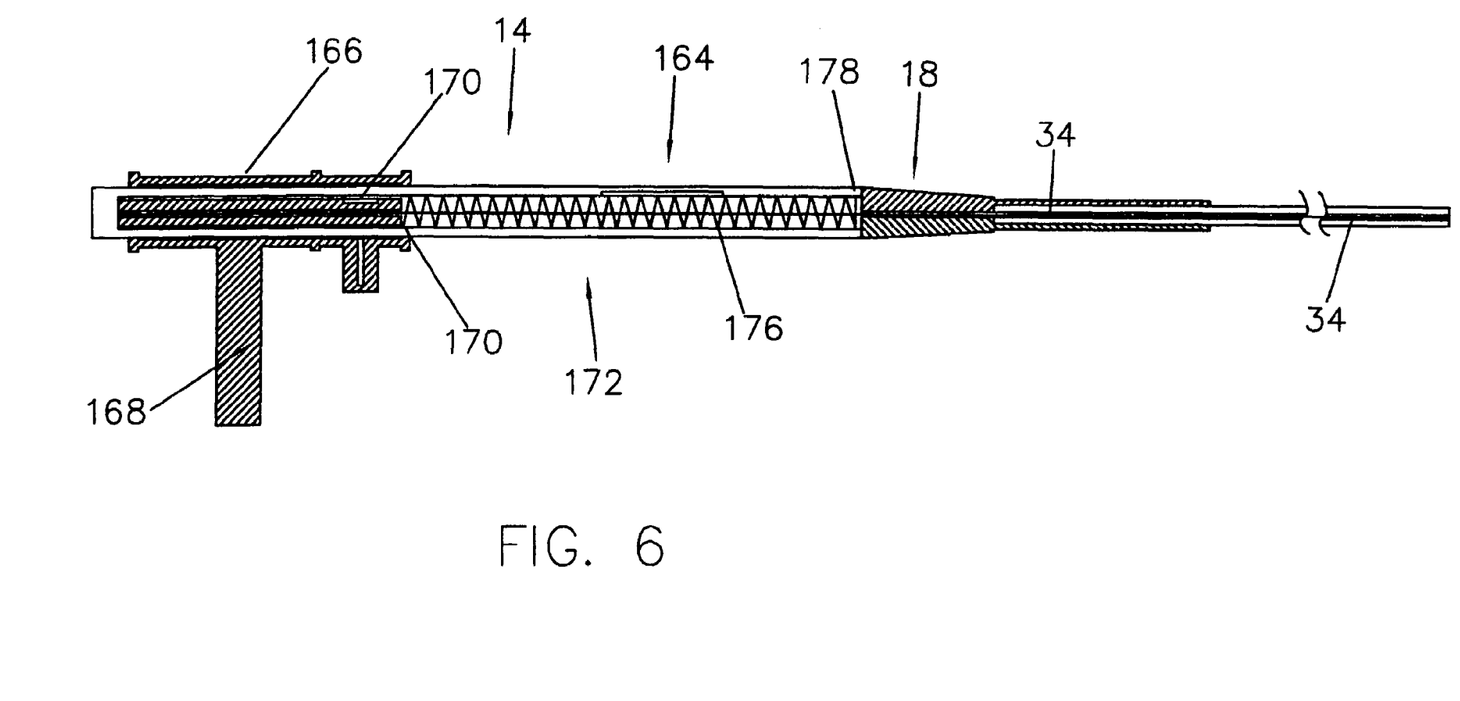
FIG. 6 is a partial cross-sectional top view of the alternate snare positioning assembly of the present invention in the first position.
Figure 7:
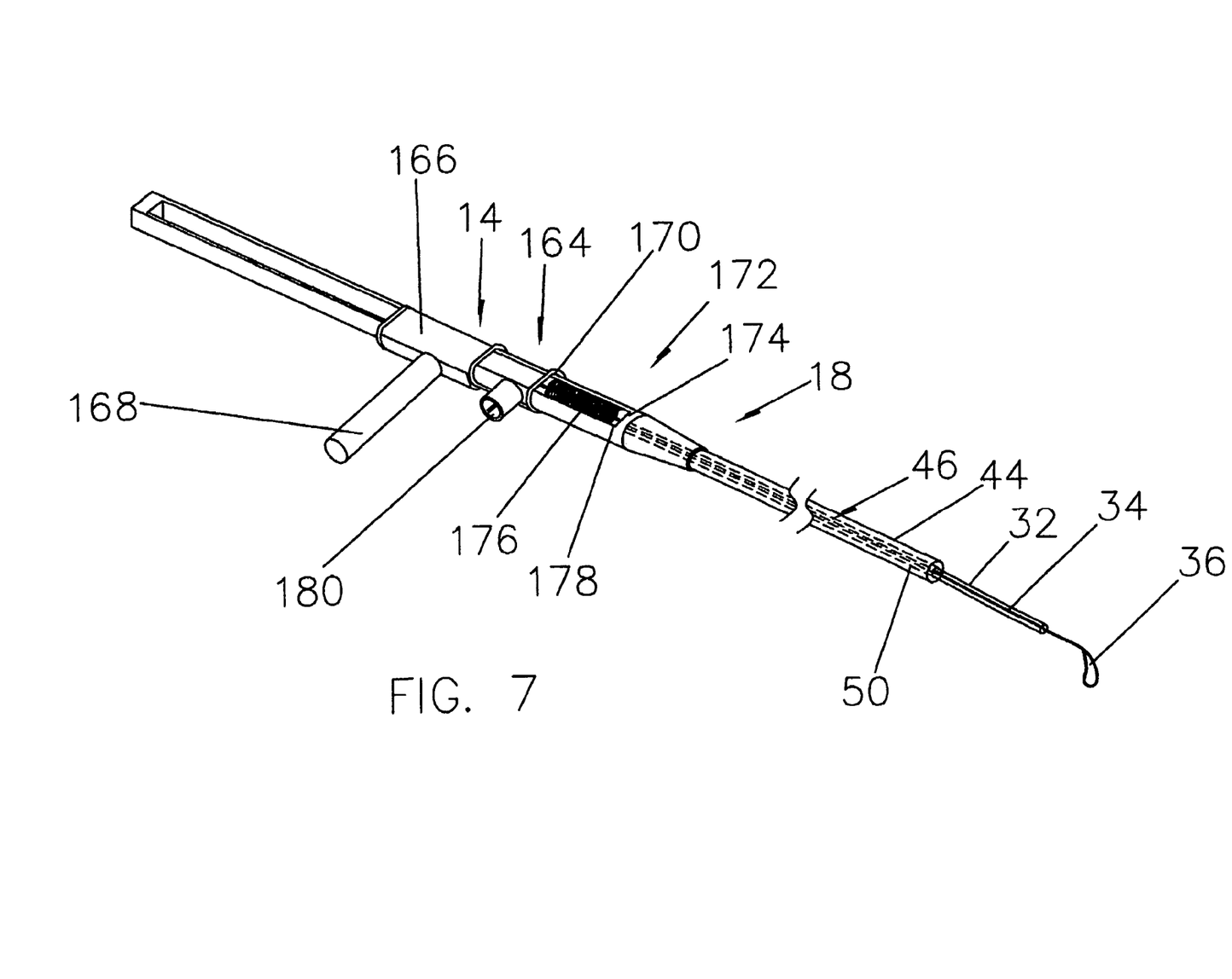
FIG. 7 is a perspective view of the alternate snare positioning of the present invention in the second position.

FIGS. 5 through 7 show an alternate embodiment of the snare positioning assembly 14. Corresponding structural elements are numbered as in FIGS. 1 through 3. The snare positioning assembly 14 comprises a positioning slide generally indicated as 164 comprising a slide 166 including a push or finger tab 168 formed on the side thereof and a bias stop or shoulder 170 and a hollow snare support generally indicated as 172 having a snare channel 174 formed therethrough to slidingly receive a portion of the polyp snare 20 therein to direct the polyp snare 20 into the snare aperture or opening 40 and a bias 176 such as a spring.

The bias 176 is disposed in the snare channel 174 to engage the bias stop 170 and a second bias stop 178 formed in the distal end portion of the snare channel 174 to engage opposite ends of the bias 176 to normally maintain the slide 166 in the first or retracted position as shown in FIG. 6.

The slide 166 and the polyp snare 20 are extended to position the polyp snare or loop 36 within the gastrointestinal tract of patient for removal of a polyp therefrom by moving the push or finger tab 168.

Once the polyp snare or loop 36 is properly positioned around the polyp and power applied to cut or remove the polyp, the push or finger tab 168 is released. The bias 176 retracts the slide 166 withdrawing the polyp snare or loop 36 and polyp from the patient. Power or current is supplied to the polyp loop 36 fed through connector 180.

It will thus be seen that the objects set forth above, among those made apparent from the preceding description are efficiently attained and since certain changes may be made in the above construction without departing from the scope of the invention, it is intended that all matter contained in the above description or shown in the accompanying drawing shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

What is claimed is:

1. An electrosurgical device for use with an electrosurgical generator to remove a polyp from a gastrointestinal tract of a patient, the electrosurgical device comprising:
    a hand piece including a housing connected to an operator handle and a snare support member attached to the housing;
    a snare support comprising a proximal elongated hollow base member mounted on a distal end portion of said snare support member, the proximal elongated hollow base member including at least one elongated side wall forming an elongated channel extending through the proximal elongated hollow base member to a distal open end of the proximal elongated hollow base member, the proximal elongated hollow base member further including a snare aperture formed through the at least one elongated side wall of the proximal elongated hollow base member, the snare aperture directed at an angle with respect to the distal open end, the snare support further comprising a distal flexible elongated snare guide having a snare channel formed therethrough to slidably receive in the snare channel at least a first portion of a polyp snare, the distal flexible elongated snare guide being affixed to a distal end portion of said proximal elongated hollow base member;
    said polyp snare comprising an electrically nonconductive sheath having an electrically conductive snare wire at least partially disposed therein and terminating in a snare loop;
    a snare positioning assembly mounted on an exterior side surface of said snare support member adjacent said snare aperture, said snare positioning assembly having a longitudinal axis that is offset from and parallel to a longitudinal axis of said snare support member and coupled to said polyp snare to selectively move said polyp snare between an extended position and a retracted position through said snare aperture such that said electrically nonconductive sheath and said electrically conductive snare wire extend from said snare positioning assembly through said snare aperture into an interior of said proximal elongated hollow base member and through said snare channel of said distal flexible elongated snare guide to a distal end portion thereof; and
    a switch assembly coupled to the electrosurgical generator, the snare positioning assembly, and the electrically conductive snare wire, the switch assembly being configured to selectively energize the electrosurgical generator and to selectively operate said snare positioning assembly to move said polyp snare from said retracted position to said extended position such that said snare loop encircles the polyp to be removed from the gastrointestinal tract of the patient, the switch assembly being further configured to selectively supply energy from the electrosurgical generator to said snare loop to cut the polyp from the gastrointestinal tract and to move said polyp snare from the extended position to said retracted position once the polyp is cut.

2. The electrosurgical device of claim 1, wherein said switch assembly comprises a switch pad to operatively support an electrosurgical generator control switch to selectively activate the electrosurgical generator, a snare positioning switch to selectively control operation of said snare positioning assembly to extend and retract the electrically conductive snare wire and said snare loop, and a polyp cutting switch to selectively feed current through said electrically conductive snare wire and said snare loop when disposed in surrounding relationship relative to the polyp to be removed from the gastrointestinal tract.

3. The electrosurgical device of claim 1, wherein said snare positioning assembly comprises a drive motor operatively coupled to a positioning slide by an intermediate drive mechanism.

4. The electrosurgical device of claim 3, wherein said positioning slide comprises a slide rack including a plurality of teeth formed on an upper surface thereof and said proximal elongated hollow base member having a snare channel formed therethrough to slidingly receive at least a second portion of said polyp snare when said polyp snare is directed into said snare aperture.

5. The electrosurgical device of claim 4, wherein said intermediate drive mechanism comprises a first drive section and a second drive section disposed to operatively engage each other to extend and retract said positioning slide and said polyp snare through said snare channel of said proximal elongated hollow base member and said snare channel of said distal flexible elongated snare guide to position said snare loop within the gastrointestinal tract of the patient for removal of the polyp therefrom.

6. The electrosurgical device of claim 5, wherein said first drive section comprises a first drive gear coupled to said drive motor by a drive shaft and said second drive section comprises a second drive gear in operative engagement with said first drive gear and a third drive gear coupled thereto by a connecting shaft in operative engagement with said plurality of teeth of said slide rack to move said positioning slide and said polyp snare in response to operation of said drive motor to extend and retract said polyp snare through said snare aperture, said snare channel of said proximal elongated hollow base member, and said snare channel of said distal flexible elongated snare guide.

7. An electrosurgical device comprising:
a housing having a longitudinal axis;
an operator handle attached to the housing, the operator handle having a longitudinal axis substantially perpendicular to the longitudinal axis of the housing;
a snare support member attached to a distal end of the housing, the snare support member having a longitudinal axis substantially aligned with the longitudinal axis of the housing;
a snare positioning assembly mounted on an exterior surface of the snare support member, the snare positioning assembly having a longitudinal axis substantially parallel with and offset from the longitudinal axis of the snare support member, the snare positioning assembly having a first channel running therethrough;
a base member attached to a distal end of the snare support member, the base member having a longitudinal axis substantially aligned with the longitudinal axis of the snare support member, the base member having a second channel running therethrough;
an aperture formed through a side wall of the base member from an exterior of the base member to the second channel running through the base member, the aperture having a longitudinal axis substantially perpendicular to the longitudinal axis of the base member;
a flexible snare guide attached to a distal end of the base member, the flexible snare guide having a third channel running therethrough;
a polyp snare comprising an electrically nonconductive sheath and an electrically conductive snare wire, the electrically conductive snare wire being at least partially disposed within the electrically nonconductive sheath and terminating in a snare loop at a distal end of the electrically conductive snare wire;
wherein the polyp snare extends at least through the first channel of the snare positioning assembly, to the exterior of the base member, through the aperture, through the second channel of the base member, and through the third channel of the flexible snare guide.

8. The electrosurgical device of claim 7, wherein the snare positioning assembly is configured to move the polyp snare between an extended position and a retracted position.

9. The electrosurgical device of claim 8, further comprising a switch assembly coupled to an electrosurgical generator, the snare positioning assembly, and the electrically conductive snare wire, wherein the switch assembly is configured to control the snare positioning assembly to move the polyp snare from the retracted position to the extended position.

10. The electrosurgical device of claim 9, wherein, in the extended position, the snare loop is configured to encircle a polyp to be removed from a gastrointestinal tract of a patient, and wherein the switch assembly is configured to supply energy from the electrosurgical generator to the snare loop to cut the polyp from the gastrointestinal tract.

11. The electrosurgical device of claim 9, wherein the switch assembly comprises:
an electrosurgical generator control switch configured to selectively activate the electrosurgical generator;
a snare positioning switch configured to selectively control operation of the snare positioning assembly to extend and retract the electrically conductive snare wire; and
a polyp cutting switch configured to selectively feed current through the electrically conductive snare wire to the snare loop.

12. The electrosurgical device of claim 7, wherein said snare positioning assembly comprises a drive motor operatively coupled to a positioning slide by an intermediate drive mechanism.

13. The electrosurgical device of claim 12, wherein the positioning slide comprises a slide rack having a plurality of teeth formed on an upper surface thereof.

14. The electrosurgical device of claim 12, wherein the intermediate drive mechanism comprises a first drive section engaged with a second drive section and configured to extend and retract the positioning slide to thereby extend and retract the polyp snare within the first channel of the snare positioning assembly, within the aperture, within the second channel of the base member, and within the third channel of the flexible snare guide.

15. The electrosurgical device of claim 14, wherein the first drive section comprises a first drive gear coupled to the drive motor by a drive shaft and the second drive section comprises a second drive gear in operative engagement with the first drive gear and a third drive gear coupled thereto by a connecting shaft in operative engagement with the plurality of teeth of the slide rack to move the positioning slide and polyp snare in response to operation of the drive motor to extend and retract the polyp snare through the snare aperture, base member, and flexible snare guide.

16. An electrosurgical device comprising:
a snare support member;
a snare positioning assembly mounted on an exterior surface of the snare support member, the snare positioning assembly having a longitudinal axis substantially parallel with and offset from a longitudinal axis of the snare support member;
a base member attached to a distal end of the snare support member, the base member having a longitudinal axis substantially aligned with the longitudinal axis of the snare support member;
an aperture formed through a side wall of the base member, the aperture having a longitudinal axis substantially perpendicular to the longitudinal axis of the base member; and
a polyp snare extending through a first channel of the snare positioning assembly, through the aperture, and through a second channel of the base member.

17. The electrosurgical device of claim 16, further comprising a flexible snare guide attached to a distal end of the base member, the flexible snare guide having a third channel running therethrough, wherein the polyp snare further extends through the third channel of the flexible snare guide.

18. The electrosurgical device of claim 16, wherein the polyp snare comprises an electrically nonconductive sheath and an electrically conductive snare wire, the electrically conductive snare wire being at least partially disposed within the electrically nonconductive sheath and terminating in a snare loop at a distal end of the electrically conductive snare wire.

19. The electrosurgical device of claim 18, wherein the snare positioning assembly is configured to move the polyp snare between an extended position and a retracted position.

20. The electrosurgical device of claim 19, further comprising a switch assembly coupled to an electrosurgical generator, the snare positioning assembly, and the electrically conductive snare wire;
- wherein the switch assembly is configured to control the snare positioning assembly to move the polyp snare from the retracted position to the extended position and vice versa;
- wherein, in the extended position, the snare loop is configured to encircle a polyp to be removed from a gastrointestinal tract of a patient; and
- wherein the switch assembly is configured to supply energy from the electrosurgical generator to the snare loop to cut the polyp from the gastrointestinal tract.

* * * * *